United States Patent
Guieze

Patent Number: 6,148,914
Date of Patent: Nov. 21, 2000

[54] SAMPLING HYDROCARBONS IN A WELL USING A FLEXIBLE BAG

[75] Inventor: Paul B. Guieze, Fontenailles, France

[73] Assignee: Schlumberger Technology Corporation, Houston, Tex.

[21] Appl. No.: 08/959,600

[22] Filed: Oct. 28, 1997

[51] Int. Cl.[7] ................................................ E21B 49/08

[52] U.S. Cl. .................... 166/264; 166/163; 166/165; 175/59; 73/152.23; 73/864.61; 73/864.62

[58] Field of Search .................. 73/152.23, 152.24, 73/152.28, 864.61, 864.62, 864.63; 166/163, 165, 264; 175/59

[56] References Cited

U.S. PATENT DOCUMENTS

| | | | |
|---|---|---|---|
| 2,223,785 | 12/1940 | Hassler | 166/264 |
| 3,793,887 | 2/1974 | Anderson et al. | 73/863.03 |
| 4,766,955 | 8/1988 | Petermann | 166/167 |
| 4,846,364 | 7/1989 | Boe | 220/4.16 |
| 5,146,998 | 9/1992 | Cordry et al. | 175/21 |
| 5,437,201 | 8/1995 | Krueger | 73/864.35 |
| 5,522,272 | 6/1996 | Vecere et al. | 73/864.62 |
| 5,901,788 | 5/1999 | Brown et al. | 166/264 |

FOREIGN PATENT DOCUMENTS

| | | |
|---|---|---|
| 898193 | 4/1972 | Canada . |
| 2132799 | 3/1996 | Canada . |
| 2 655 145 A1 | 5/1991 | France . |
| 2 203 117 | 10/1988 | United Kingdom . |
| 2 264 172 | 8/1993 | United Kingdom . |
| WO 90/08308 | 7/1990 | WIPO . |
| WO 91/09207 | 6/1991 | WIPO . |

OTHER PUBLICATIONS

DuPont Teflon(R)—Industrial Applications, www.dupont.com/teflon/industrial/6405.html.

*Primary Examiner*—Eileen D. Lillis
*Assistant Examiner*—John Kreck
*Attorney, Agent, or Firm*—John J. Ryberg; Brigitte L. Jeffery

[57] ABSTRACT

To take a sample of liquid and/or gaseous hydrocarbon at the surface or down an oil well, use is made of a flexible bag suspended by a tube from a top region of a wall of a closed receptacle. The bag and the tube are made of a flexible material that is leakproof and inert relative to the sample to be taken, such as a cross-linked polymer. The volume of sample admitted into the bag is controlled so as to avoid stretching the wall of the bag.

6 Claims, 2 Drawing Sheets

SAMPLING HYDROCARBONS IN A WELL USING A FLEXIBLE BAG

TECHNICAL FIELD

The invention relates to a method of taking and storing a liquid and/or gaseous hydrocarbon sample, and usable equally well down an oil well or at the surface.

The invention also relates to a device implementing the method.

STATE OF THE ART

Before operating an oil well, it is the practice to take samples of the fluid present down the well in order to be able subsequently to perform measurements and analyses on the samples, once they have been raised to the surface.

While an oil well is in operation, samples of the hydrocarbon effluent are also taken at regular intervals from various points of the surface installation. The samples taken are likewise transferred to a laboratory where they are subjected to measurement and analysis.

Whatever the location from which the sample is taken, it is essential for the sample that reaches the laboratory to be completely representative of the sample taken, at least with respect to composition. Thus, the proportions of the various chemical elements present in a petroleum fluid must remain unchanged between the location where the sample is taken and the laboratory.

In practice, this constraint is particularly difficult to satisfy in full, as can be seen on analyzing presently-existing sampling devices.

In general, all such existing devices are made on the same principle which consists in defining, within a hermetically closed receptacle, a sealed chamber that contains a driving fluid under pressure and a volume suitable for receiving the sample. To take the sample, the driving fluid is progressively exhausted from the chamber so as to suck a sample of hydrocarbon into the volume provided for that purpose.

A first known technique implementing that principle consists in using mercury as the driving fluid and in sucking the sample directly into the volume left above the mercury extracted from the chamber. The hydrocarbon sample and the driving fluid are thus directly in contact with each other, which is possible because of the immiscible nature of mercury and because of the large difference in the densities of the two fluids present.

Nevertheless, mercury is a dangerous substance and use thereof is now considered undesirable. Also, direct contact between the two fluids makes it impossible to guarantee that the samples taken are indeed representative, particularly when they contain $H_2S$.

Another known technique implementing the above-outlined principle is described in patent applications FR-A-2,655,145 and GB-A-2,264,172. In that case, the receptacle is in the form of a cylinder and the volume for receiving the hydrocarbon sample is separated from the chamber that contains the driving fluid by a piston slidable in the cylinder.

That configuration makes it possible to use any non-compressible driving fluid that is not dangerous for the environment. For example, it is possible to use a mixture of water and glycol as the driving fluid if the device is used on the surface, while the fluid used is generally hydraulic oil when the device is intended for taking samples downhole.

That device nevertheless suffers from a certain number of problems associated mainly with the presence of the piston and the need to provide tightness between the two fluids.

Thus, experience shows that sealing gaskets are always slightly permeable. Limited chemical migration is therefore inevitable which has the effect of altering subsequent analyses performed on the sample taken, particularly if the sample is stored prior to being transferred to the laboratory.

Also, the piston and the receptacle are generally made of stainless steel. Unfortunately, that material is not completely inert relative to certain substances that are frequently present in hydrocarbons, such as $H_2S$. Consequently, when such substances are present in very small quantities in the sample, there is a risk that they will disappear completely by reacting with the steel of the piston and of the receptacle. That constitutes a second reason why the results of analyses performed on the sample are not truly representative of the sample taken.

Also, friction between the cylinder and the sealing rings carried by the piston leads inevitably to a pressure difference across the piston. This pressure difference can give rise to a change of phase if the fluid being sampled is very close to its saturation pressure. The representativeness of the analyzed sample can thus likewise be altered with respect to the proportions of the various phases it contains.

Finally, a piston device as described in documents FR-A-2,655,145 and GB-A-2,264,172 is unusable in practice when the sample to be taken is gaseous. That would require the device to be given dimensions such as to make the cost thereof unacceptable, given the difficulties involved in obtaining satisfactory tightness between two fluids around a large diameter.

A third known technique implementing the above-outlined principle consists in keeping the sample separate from the driving fluid by means of a deformable membrane whose rim is held captive between two portions of the receptacle. That technique is illustrated in particular by U.S. Pat. No. 4,846,364.

As when a piston is used to keep the two fluids apart, that technique makes it possible to use a driving fluid of any kind, whether miscible or immiscible with the fluid to be sampled and regardless of the difference in density between the two fluids.

Nevertheless, the use of a device having a deformable membrane suffers from numerous drawbacks, stemming both from the nature of the material used for making the membrane and also from the technique proper, since it requires the rim of the membrane to be sealingly clamped between two portions of the receptacle.

Thus, the materials proposed for making the membrane are either a metal, or a more flexible material such as rubber.

When a metal is used, implementing the device is particularly lengthy and complex since the membrane must be changed on each use and it deforms very slowly. In addition, the metals used (lead and aluminum) are not inert relative to the sampled fluid, such that the analyses performed are altered. Also, the pressure difference across the membrane varies and is very large, which can lead to a change of phase in the fluid sample if it happens to be close to its saturation pressure. In addition, it is very difficult to ensure tightness between the membrane and the receptacle since there is metal-on-metal contact.

When rubber is used to make the membrane of the device described in U.S. Pat. No. 4,846,364 that material is not completely inert relative to the sampled petroleum fluid, which fluid also remains in contact with the steel of the receptacle. In addition, the pressure difference across the two faces of the membrane remains high enough to run the risk of causing a change of phase in the sampled fluid.

Document WO-A-91/09207 proposes a variant of the device described in U.S. Pat. No. 4,846,364. In that case, the deformable membrane is in the form of a tube whose ends are fixed to two rigid cylindrical endpieces connected to each other by a shape member that is also rigid, of channel section, and placed inside the deformable tube. As in the preceding document, the tube is made of a deformable metal such as lead, or else of rubber.

In that device, the sample comes into contact with materials that are not inert (lead or rubber for the tube, steel for the endpieces and the shape member). The sample as analyzed is therefore not totally representative of the sample as taken. In addition, the problems associated with the nature of the material used for the deformable tube are identical to those mentioned above with respect to U.S. Pat. No. 4,846,364 (risk of a phase change due to pressure difference, and implementation that is lengthy and complex).

SUMMARY OF THE INVENTION

The invention mainly provides a method of taking a sample of hydrocarbon that enables such a sample to be taken in a manner that is particularly simple and economical, regardless of whether the sample is liquid, gaseous, or a mixture of liquid and gas, and that enables the sample to be taken from any location, i.e. downhole or on the surface, and that makes this possible in such a manner that the sample as analyzed is truly representative of the sample as taken, with respect to composition.

According to the invention, there is provided a method of taking a hydrocarbon sample, wherein the sample is put into a sampling bag that is flexible, leakproof, and chemically inert relative to the sample to be taken, the bag being placed in a leakproof chamber defined by a wall of a receptacle through which there passes a sampling tube connecting the bag to the wall, with a controlled volume of driving fluid interposed between the bag and the wall being removed from the chamber, said volume being such that the bag is not stretched.

The use of a flexible and leakproof bag for collecting the sample makes it particularly simple to obtain sealing. It is possible to use this method regardless of the nature of the fluid to be taken (liquid, gas, or a mixture thereof).

In addition, the use of a flexible sampling bag for taking a sample of hydrocarbon also enables the pressure difference between the two fluids to be made negligible, thereby avoiding any risk of the sample changing phase while it is being taken.

In addition, the sample to be taken comes into contact only with the flexible material of the bag. By selecting this material so that it is inert relative to the fluid constituting the sample, any risk of the nature of said fluid being modified by reaction between the fluid and the materials with which it comes into contact is avoided. The use of a flexible bag makes it particularly simple to achieve this result without it being necessary to machine or treat the inside of the receptacle in any special way. This characteristic also makes it possible to keep dead volumes down to a minimum.

Preferably, the sampling tube is made of the same material as the bag. This material may be constituted, in particular, by a cross-linked polymer, e.g. of the polyether ether ketone (PEEK) type. Such a material also has the advantage of withstanding high temperature.

It should also be observed that the characteristics of the method of the invention make it possible to take a sample equally well down an oil well as at the surface.

The invention also provides a device for taking a hydrocarbon sample, the device being characterized by the fact that it comprises: a receptacle having a wall defining an internal leakproof chamber; a sampling bag that is initially empty, flexible, leakproof, and chemically inert relative to the sample to be taken, and placed inside said chamber, being separated from the wall by a driving fluid; a sample-taking first passage and a driving fluid inlet and outlet second passage each passing through the wall of the receptacle; and a sampling tube connecting the bag to the first passage.

In a preferred embodiment of the invention, the bag is made of two flexible films that are initially plane and bonded together in a peripheral region. One end of the sampling tube can then be bonded to a first one of the flexible films within the above-mentioned peripheral region and in the vicinity thereof. The sampling tube is then bent through a right angle close to its end that is bonded to the first flexible film.

In the preferred embodiment of the invention, the two flexible films forming the bag are two identical rectangular films.

In order to enable the temperature of the sample taken to be controlled, heater means may be provided within the receptacle.

Pressure may also be maintained by causing the leakproof chamber to communicate with a gas under pressure, such as nitrogen.

BRIEF DESCRIPTION OF THE DRAWINGS

A preferred embodiment of the invention is described below by way of non-limiting example and with reference to the accompanying drawings.

DETAILED DESCRIPTION OF A PREFERRED EMBODIMENT

Figure 1:
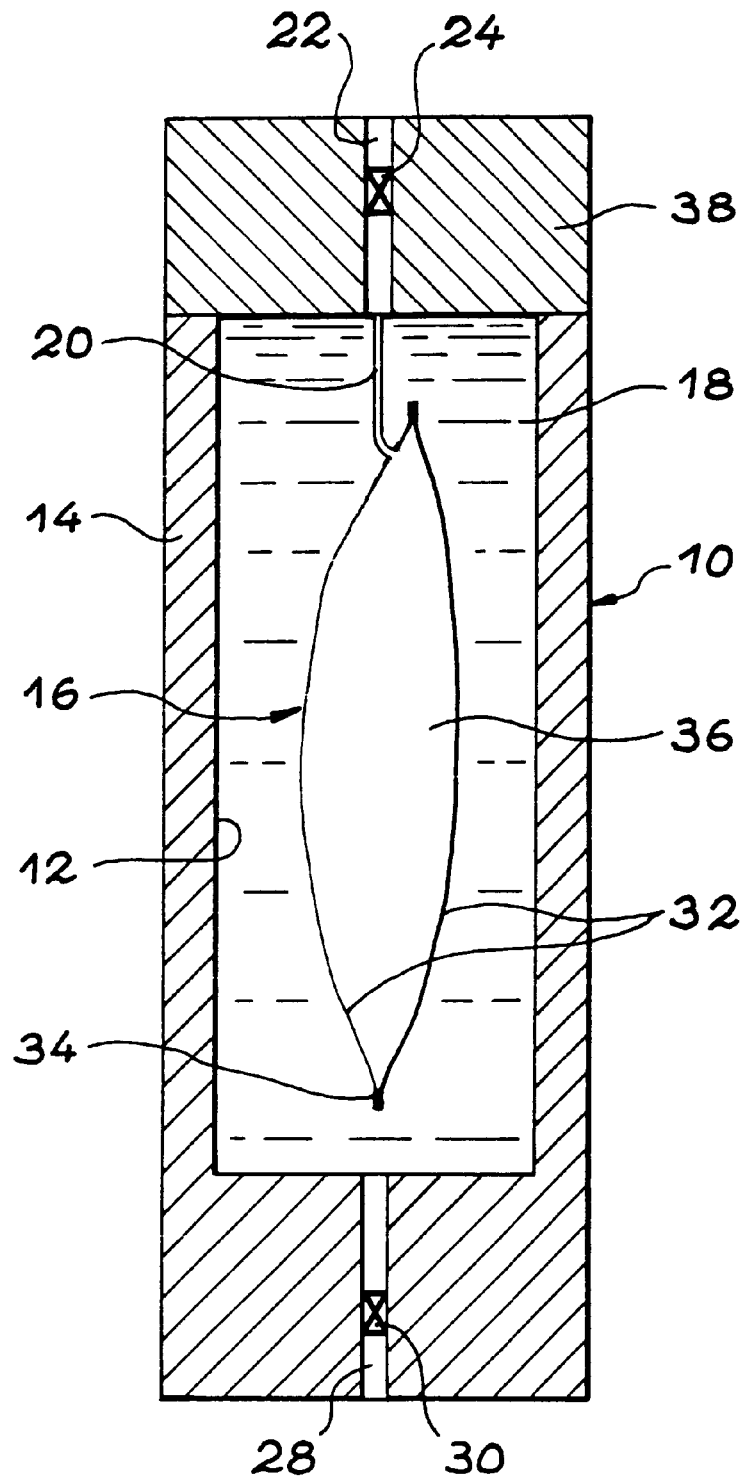
FIG. 1 is a longitudinal section view which shows, in highly diagrammatic manner, a sample-taking device of the invention.

According to the invention, the device for taking a hydrocarbon sample whose preferred embodiment is shown diagrammatically in FIG. 1, can be used equally well for taking a fluid sample down an oil well as on the surface, and can do so regardless of the nature of the fluid phases (liquid oil, water, and/or gas).

Given its wide applicability, the device of the invention can be used equally well for taking a hydrocarbon sample from an oil well, from a pipe, at the outlet from a tank, or from apparatus such as a separator. Where necessary it may comprise a plurality of identical stages so as to enable a plurality of samples to be taken successively at intervals of time or from distinct locations. The device also makes it possible to convey the sample(s) to the laboratory for analysis, possibly after storage and/or transport.

The sampling device of the invention comprises a receptacle 10 which is rigid and suitable for withstanding high temperature and pressure. The receptacle 10 may be made of stainless steel, in particular. Its wall 14 defines an internal sealed chamber 12. It should be observed that the surface of the wall 14 defining the chamber 12 does not need to be accurately machined and does not require any special treatment. The shape and the dimensions of the receptacle 12 depend essentially on the location from which the sample is to be taken and on the nature of the fluid to be sampled.

Thus, when the device is intended for taking a sample downhole, the receptacle 10 is in the form of an elongate cylinder whose outside diameter is selected to enable it to be lowered down the well and then raised.

When sampling is performed on the surface, the shape of the receptacle 10 can be arbitrary and its dimensions depend on the nature of the sampled fluid. Thus, the dimensions of the receptacle 10 will be larger when the sample to be taken is gaseous than when it is in the form of a liquid.

For manufacturing reasons, the receptacle 10 and its sealed chamber 12 are advantageously cylindrical under all circumstances. While the device is in use, the axis of the receptacle 10 normally extends vertically, as shown in FIG. 1.

The sampling device of the invention also comprises a sampling bag 16 that is flexible and leakproof, and that is placed inside the chamber 12.

The function of the sampling bag 16 is to receive the hydrocarbon sample that is taken, and it is made of a leakproof material whose flexibility enables it to deform freely without creating any significant pressure difference between the inside and the outside of the bag. In addition, the material from which the sampling bag 16 is made is advantageously selected so as to be chemically inert relative to the sample that is to be taken.

When sampling conditions justify it, and in particular when the device is used for taking samples downhole, the material from which the sampling bag 16 is made is also capable of withstanding high temperatures, up to a temperature exceeding the maximum ambient temperature to which the device is to be subjected.

A material that enables all of the above requirements to be satisfied simultaneously is constituted by cross-linked polymers, and particular mention may be made of the material known as polyether ether ketone (PEEK).

To enable the sampling device of the invention to be implemented, the volume of the chamber 12 outside the bag 16 is initially filled with a driving fluid 18. In known manner, the nature of the driving fluid depends on the location at which sampling is performed. Thus, the driving fluid is generally constituted by a hydraulic oil when sampling is performed downhole, whereas it is generally constituted by a mixture of oil and glycol when sampling is performed on the surface.

To complete this description of the sampling device of the invention, it is appropriate to describe the means whereby the sampling bag 16 is mechanically connected to the wall 14 of the receptacle 10 and also the means for controlling ingress and egress of the sample into and out from the sampling bag 16, and also the means for controlling ingress and egress of driving fluid 18 into and out from the chamber 12.

Figure 2:
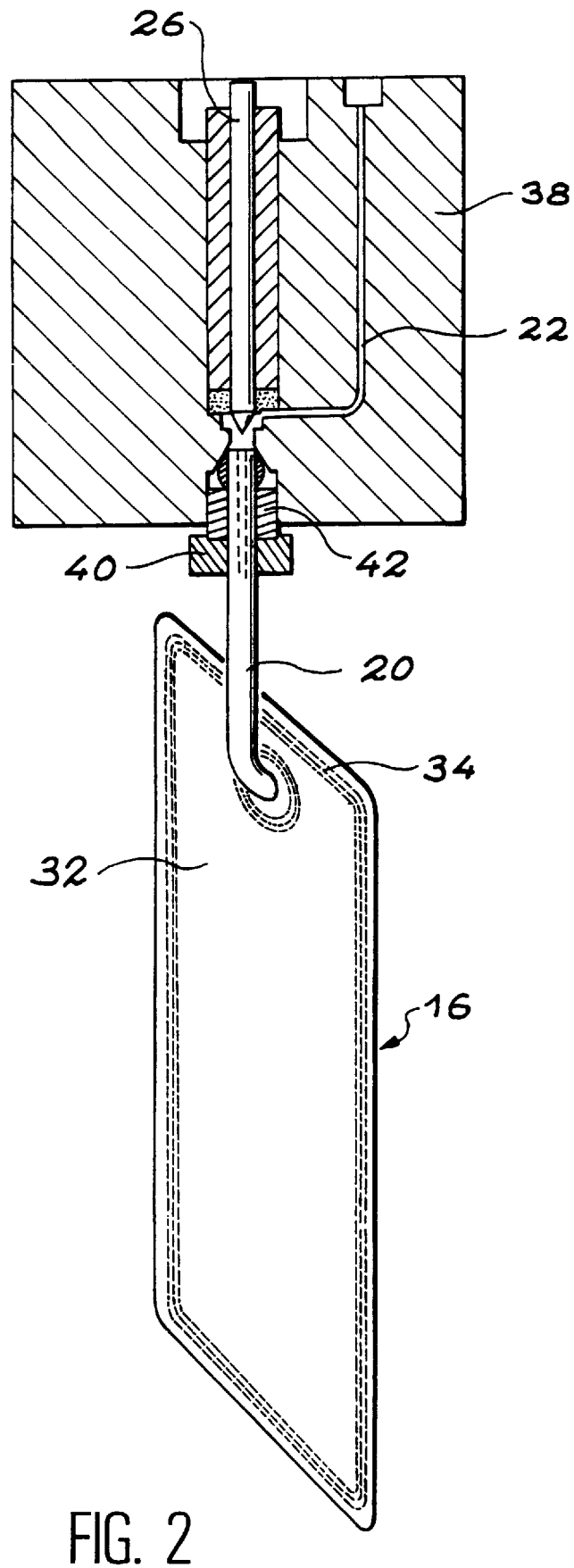
FIG. 2 is partially in section and partially a perspective view, showing a detail of the FIG. 1 device.

As shown more clearly in FIG. 2, the sampling bag 16 is mechanically connected to one of the walls of the receptacle 10 by a sampling tube 20 which also serves for ingress and egress of the sample. The sampling tube 20 is connected in sealed manner at a first end to the sampling bag 16 so as to open out to the inside thereof, and its opposite end is connected to the horizontal top region of the wall 14 so that the bag 16 hangs by gravity inside the chamber 12.

The sampling tube 20 is advantageously made of a material that is identical to that of the sampling bag 16, i.e. preferably of a cross-linked polymer such as polyether ether ketone (PEEK).

This characteristic serves to avoid any chemical reaction between the sample that has been taken and the sampling tube, and it also ensures that the tube can withstand high temperature.

In order to ensure that the sample is conveyed all the way to the bag 16 during sampling, and also to ensure that said sample is subsequently expelled from the device, the horizontal top region of the wall 14 of the receptacle 10 has a through passage 22 for sample-taking purposes. The bottom end of the passage 22 communicates with the top end of the sampling tube 20 while the top end of the passage 22 opens out to the outside of the receptacle 10.

As shown diagrammatically in FIG. 1, and in greater detail in FIG. 2, a valve 24 is placed in the sample-taking passage 22 so that said passage is normally closed in sealed manner, except during periods when a sample is being taken or is being expelled.

The valve 24 may be made in any conventional manner without going beyond the ambit of the invention. By way of example, FIG. 2 shows a valve 24 which is opened and closed under the control of a sliding rod 26 whose end constituting a valve member normally closes a valve seat formed in the passage 22 in line with the top portion of the sampling tube 20. It should be observed that the chemically inert nature of the device of the invention relative to the sample taken can be further improved by making the wall portion through which the passage 22 is formed, and also the elements constituting the valve 24, out of a material that is chemically inert, or by coating the surfaces thereof that are liable to come into contact with the sample in such a material.

Also, as shown diagrammatically in FIG. 1, the driving fluid 18 is injected into the chamber 12 and is removed therefrom in conventional manner via an inlet and outlet passage 28 for the driving fluid, which passage passes through the wall 14 of the receptacle 10. The passage 28 is controlled by a valve 30 which may be made in any conventional manner without going beyond the ambit of the invention.

In the preferred embodiment shown more precisely in FIG. 2, the sampling bag 16 is made up of two flexible films 32 which are initially plane and of very small thickness (e.g. about 25 $\mu$m to about 50 $\mu$m), and having identical rectangular shapes. These two flexible films are bonded together in a peripheral region as represented by bonding line 34 so as to define an inside volume 36 that is entirely enclosed between the two films. More precisely, the volume 36 is initially reduced to zero by the pressure that is applied to the outside surfaces of the films 32 by the driving fluid 18.

In this preferred embodiment, the tube 20 is L-shaped, with its substantially vertical long branch being connected to the top region of the wall 14 of the receptacle 10 and with its substantially horizontal short branch being connected to one of the flexible films 32 at a point inside the peripheral region that includes the bonding line 34, and that is close thereto. The connection between this short branch and the flexible film 32 is also formed by bonding such that the sampling tube 30 communicates with the volume 36 defined inside the sampling bag 16.

As already mentioned, when the device is ready for use to take a sample, the inside volume of the sampling bag 16 is empty under the effect of the pressure exerted on the flexible films 32 by the driving fluid 18 which then completely fills the chamber 12. To take a sample, the valve 24 is opened so as to put the inside volume of the sampling bag 16 into communication with the outside, after which the valve 30 is opened so as to enable a predetermined and fully controlled volume of driving fluid 18 to be removed from the chamber 12. This volume accurately determines the volume of the hydrocarbon sample taken into the sampling bag 16. This volume is determined so that the deformation of the two films from which the sampling bag 16 is made cannot under any circumstances cause the bag to reach its inflated volume. In other words, the working area of the flexible films 32, i.e. the area thereof defining the volume of the sample taken, must remain substantially unchanged from the beginning to the end of the sample-taking operation. Otherwise the films 32 would be subjected to traction stress which they are unsuitable for withstanding given that they are very thin. It should be observed that this requirement to control the volume of driving fluid 18 removed from the chamber 12 is associated with the negligible nature of the pressure gradient between the sample fluid and the driving fluid.

This accurate control of the volume of driving fluid 18 removed from the chamber 12 can be provided in particular by putting said chamber 12 into communication with a receiver chamber having exactly the desired volume. This solution can be applied equally well downhole and at the surface.

When a sample is taken at the surface, the volume of driving fluid 18 removed from the chamber 12 during sampling may also be controlled by other means, e.g. by visually monitoring the volume removed from the chamber 12, in particular by means of a graduated test tube, or by using an electrically controlled valve to replace the valve 30 and provide timed opening of the passage 28.

As already observed, there is no need for the machining of the chamber 12 to be accurate and there is no need for its surface to be treated. This contributes to making the cost of the device particularly low, whatever the type of fluid that is to be sampled.

Also, the sampling bag 16 can be reused, i.e. the same bag can be used without being disassembled to take a large number of samples. This characteristic shortens the implementation procedure to a great extent since it is rarely necessary to disassemble the device between taking two consecutive samples.

In addition, when it is necessary to change the bag 16, the procedure for doing so is particularly simple. Thus, it suffices for the operator to remove the cover 38 (FIGS. 1 and 2) constituting the top region of the wall 14 and then to disconnect the sampling tube 20 from the cover. This disconnection can easily be performed by loosening a nut 40 used for connecting the tube 20 in sealed manner to the passage 22 via a packing gland 42. A new bag 16 fitted with a new sampling tube 20 is then installed in the same manner, after which the receptacle 10 is reclosed.

The rate at which samples can be taken is also increased because of the highly flexible nature of the thin films 32 constituting the bag 16, which bag deforms immediately while a sample is being taken, unlike devices that include a piston.

Given that the pressure across the wall of the sampling bag 16 is substantially in equilibrium, any risk of accidental phase change in the sampled fluid is eliminated. Further, the chemically inert and temperature-resisting nature of the material constituting the walls of the bag 16 has the effect of preventing any modification to the composition of the sample as taken. The sample as analyzed is therefore truly representative of the sample as taken.

It should be observed that the representativeness of the sample as analyzed compared with the sample as taken is likewise ensured even after the sample has been stored for a long period of time in the device.

It should also be observed that the device of the invention makes it possible to transfer for analysis purposes either the entire sample as taken or else only a portion of the sample. This makes it possible to avoid using an intermediate storage cylinder that could cause the composition of the sample to be modified.

It would also be observed that the material used for making the sampling bag 16 is such that practically no diffusion takes place between the driving fluid and the sampled fluid. Similarly, the proposed technique makes it possible to ensure practically perfect sealing without there being any need to make use of sealing gaskets which are always permeable to some extent. There is thus practically no chemical migration between the two fluids, thereby further contributing to guaranteeing the representativeness of the sample as analyzed compared with the sample as taken.

If necessary, heater means may be provided inside the receptacle 10. This characteristic can be used in particular when the device is intended for taking samples downhole. The heater device can then compensate for the temperature drop that occurs when the device is raised to the surface. This avoids possible deposition of paraffin that would run the risk of blocking the sampling tube and consequently preventing the taken sample from being recovered.

The heater means may be constituted by any means such as heater resistances (not shown) located inside the chamber 12 around the sampling bag 16. Such heater resistances may be located, in particular, on a polyamide film lining the inside surface of the wall 14 of the receptacle 10.

When the device of the invention is used for taking samples downhole, it may also be necessary to maintain pressure inside the device, both while it is being raised to the surface and also during subsequent transport to the analysis laboratory. This can be performed in particular by then putting the chamber 12 into communication via a passage (not shown) with a tank of compressed nitrogen that sets the pressure to a desired value. This precaution then serves to avoid any asphaltenes precipitating under the effect of the composition of the liquid phase changing due to a drop in pressure.

Finally, it should be observed that the absence of a piston makes it possible to pass electric cables through the chamber 12, between the bag 16 and the wall 14 of the receptacle 10.

What is claimed is:

1. A method of taking a hydrocarbon sample of a petroleum fluid, comprising providing at a location down an oil well from which a hydrocarbon sample is to be taken, an apparatus for taking a hydrocarbon sample, said apparatus comprising a receptacle having walls defining an internal leakproof chamber, a flexible, leakproof, and chemically inert sampling bag disposed inside and sealed from said chamber, means for introducing a hydrocarbon sample into the interior of said sampling bag; and means for removing and introducing a driving liquid into said chamber, a controlled volume of a driving being interposed between the exterior of the sampling and the walls of the chamber;

drawing a volume of hydrocarbon at the location from which the sample is to be taken, though said means for introducing a hydrocarbon sample into the sampling bag by removing a predetermined volume of driving liquid from the chamber by said means for removing and introducing a driving liquid, the volume of driving liquid removed being equal to the volume of hydrocarbon drawn into the sampling bag.

2. The method of claim 1 in which the means for introducing a hydrocarbon sample into the interior of said sampling bag comprises a first passage through a wall of said chamber communicating through a sampling tube with the interior of said sampling bag, the means for introducing and removing a driving liquid into said chamber comprises a driving fluid inlet and outlet passage through the wall of said chamber, and the driving liquid is removed into a receiver chamber.

3. The method of claim 1 in which the driving liquid is removed into a receiver chamber.

4. The method of claim 3 in which the driving liquid is hydraulic oil.

5. The method of claim 1 comprising the steps of placing said leakproof chamber in fluid communication with a gas under pressure.

6. The method of claim 1 in which the driving liquid is hydraulic oil.

* * * * *